(12) United States Patent
Uchida et al.

(10) Patent No.: US 7,172,560 B2
(45) Date of Patent: Feb. 6, 2007

(54) LIVING BODY INFORMATION ACQUIRING APPARATUS AND LIVING BODY INFORMATION ACQUIRING METHOD

(75) Inventors: Shinji Uchida, Neyagawa (JP); Kazuya Kondoh, Katano (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 383 days.

(21) Appl. No.: 10/240,889

(22) PCT Filed: Apr. 4, 2001

(86) PCT No.: PCT/JP01/02914

§ 371 (c)(1),
(2), (4) Date: Mar. 17, 2003

(87) PCT Pub. No.: WO01/76485

PCT Pub. Date: Oct. 18, 2001

(65) Prior Publication Data

US 2003/0158501 A1   Aug. 21, 2003

(30) Foreign Application Priority Data

Apr. 5, 2000 (JP) ............................. 2000-103034
Aug. 7, 2000 (JP) ............................. 2000-238938

(51) Int. Cl.
*A61B 5/117* (2006.01)
*A61B 5/103* (2006.01)

(52) U.S. Cl. ..................................... 600/587
(58) Field of Classification Search ............. 600/587; 33/759, 512, 770

See application file for complete search history.

(56) References Cited

U.S. PATENT DOCUMENTS

| 6,048,323 A | * | 4/2000 | Hon ........................... 600/588 |
| 6,101,405 A | | 8/2000 | Yasuda et al. |
| 6,640,460 B1 | * | 11/2003 | Nabarro et al. ............... 33/759 |

FOREIGN PATENT DOCUMENTS

| JP | 6-189928 | | 7/1994 |
| JP | 10-314143 | | 12/1998 |
| JP | 11-47119 | | 2/1999 |
| JP | 11-239573 | | 9/1999 |
| JP | 2000-350710 | | 12/2000 |
| JP | 2000-350727 | | 12/2000 |
| JP | 2000350727 A | * | 12/2000 |
| JP | 2002282241 A | * | 10/2002 |

OTHER PUBLICATIONS

International Search Report corresponding to application No. PCT/JP01/02914 dated Jul. 10, 2001.
English translation of Form PCT/ISA/210.

* cited by examiner

*Primary Examiner*—Max F. Hindenburg
*Assistant Examiner*—Brian Szmal
(74) *Attorney, Agent, or Firm*—RatnerPrestia

(57) ABSTRACT

A conventional living body information acquiring apparatus for measuring a skinfold thickness of a living body could not fix a relative position of skinfold thickness measuring means to the living body. Thus, the present invention comprises skinfold thickness measuring means of measuring a skinfold thickness of a living body 9 composed of a light source 1 and a photodetector 2, a protruding part 3 as relative position fixing means of fixing a relative position of living body information acquiring means to the living body 9 substantially constant, and holding means 4 of holding the light source 1, the photodetector 2, and the protruding part 3.

11 Claims, 3 Drawing Sheets

LIVING BODY INFORMATION ACQUIRING APPARATUS AND LIVING BODY INFORMATION ACQUIRING METHOD

This application is a U.S. National Phase Application of PCT International Application PCT/JP01/02914.

TECHNICAL FIELD

The present invention relates to a living body information acquiring apparatus and a living body information acquiring method for acquiring living body information concerning body fat such as a degree of obesity, a body fat percentage, a skinfold thickness, and an offal fat amount.

BACKGROUND ART

As a conventional apparatus for measuring body fat, an apparatus employing a caliper method has been used for measuring a skinfold thickness by picking up the subcutaneous fat with a moderate pressure.

In addition, as another conventional apparatus for measuring body fat, an apparatus for measuring one's body weight and body height as well as measuring an electrical resistance between both of one's legs to calculate a body fat percentage from these measured values has been suggested (see Japanese Patent Laid-Open No. 6-189928). The entire disclosure of Japanese Patent Laid-Open No. 6-189928 is incorporated herein by reference in its entirety.

However, the conventional apparatus for measuring body fat described above had some problems as follows.

First, the apparatus employing the caliper method described above had some problems of causing pain upon picking up the subcutaneous fat and of bringing about variations in measured values due to fluctuations of the force for picking up the subcutaneous fat. In particular, a thickness of the subcutaneous fat which was picked up by a measuring operator subtly varied because the extent of the force application in an action of picking up the subcutaneous fat was significantly dependent on the measuring operators, so that skills were required for precisely carrying out the measurement.

Therefore, it can be considered to acquire the living body information of the living body with the use of living body information acquiring means of acquiring the living body information such as the skinfold thickness of the living body through optical measurement for example, but in such a case, it becomes necessary to provide means of allowing a distance between the living body and the living body information acquiring means to be substantially constant.

In addition, in another conventional apparatus for measuring body fat which directly measured a height of one's head position in order to measure one's body height, a hold-down part had to be raised above the top of one's head, so that a taller support base was required for supporting the hold-down part. As a consequence, this apparatus became too large to be placed within individual households.

Further, it took a little time to pull off one's socks when measuring the electric resistance between the both legs.

Still further, there was no means of measuring a skinfold thickness at an abdominal region, so that the topical information on the abdominal region could not be obtained.

DISCLOSURE OF THE INVENTION

It is an object of the present invention, considering the above described conventional problems, to provide a living body information acquiring apparatus which acquires living body information of a living body by maintaining a distance between the living body and living body information acquiring means fixed substantially constant.

It is another object of the present invention to provide a living body information acquiring method for calculating an offal fat amount of a living body.

It is another object of the present invention to provide a living body information acquiring apparatus for calculating an offal fat amount of a living body.

It is yet another object of the present invention to provide a living body information acquiring apparatus and a living body information acquiring method for specifying an obesity type of a living body.

It is yet another object of the present invention to provide a living body information acquiring apparatus for measuring an umbilicus height of a living body.

It is a further object of the present invention to provide a living body information acquiring method and a living body information acquiring apparatus for measuring a height of an umbilicus position of a living body and calculating a body fat percentage of the living body using the height of an umbilicus position.

Thus, an object of the present invention, in view of the above described conventional problems, is to provide a living body information acquiring apparatus of small size and a living body information acquiring method which can acquire living body information concerning body fat with ease and high precision and which can obtain topical information on an abdominal region, a brachial region, a femoral region, and a scapular region for example.

One aspect of the present invention is a living body information acquiring apparatus comprising living body information acquiring means acquiring living body information of a living body, relative position fixing means fixing a relative position of said living body information acquiring means to an abdominal region of said living body substantially constant, and holding means of holding said living body information acquiring means and said relative position fixing means.

Another aspect of the present invention is the living body information acquiring apparatus comprising waist measuring means measuring a circumference of waist of said living body, wherein said living body information is a skinfold thickness at a waist position of said living body, and said relative position fixing means is means fixing a distance between an umbilicus of said living body and said living body information acquiring means substantially constant.

Still another aspect of the present invention is the living body information acquiring apparatus wherein said relative position fixing means has a protruding part.

Yet still another aspect of the present invention is the living body information acquiring apparatus wherein said living body information acquiring means has a light source for measuring a skinfold thickness of a living body and a photodetector for detecting light which is outgoing from the light source and is diffusely scattered through an interior of said living body.

Still yet another aspect of the present invention is the living body information acquiring apparatus, wherein:

said relative position fixing means has a first protruding part while said holding means has a second protruding part;

a body of said holding means, said first protruding part, and said second protruding part form a space; and said living body information acquiring means is secured to the body of said holding means within said space.

A further aspect of the present invention is a living body information acquiring apparatus comprising:

waist measuring means measuring a circumference of waist of a living body;

skinfold thickness information capturing means capturing information of a skinfold thickness at a waist position of said living body; and obesity type specifying means in which an obesity type of the living body whose circumference of waist is measured by said waist measuring means is specified based on said circumference of waist measured by said waist measuring means and information about said skinfold thickness captured by said skinfold thickness information capturing means.

A still further aspect of the present invention is a living body information acquiring apparatus comprising body weight measuring means measuring a body weight of a living body and distance measuring means measuring a distance between an umbilicus of the living body and said body weight measuring means when the living body gets on said body weight measuring means.

A yet further aspect of the present invention is the living body information acquiring apparatus comprising electric resistance measuring means which is held by both hands of the living body getting on said body weight measuring means and which measures an electric resistance value of the living body.

A still yet further aspect of the present invention is the living body information acquiring apparatus comprising:

body height estimating means estimating a body height of a living body getting on said body weight measuring means, based on the distance between an umbilicus of the living body and said body weight measuring means when the living body gets on said body weight measuring means; and body fat percentage calculating means calculating a body fat percentage of said living body, based on said body weight measured by said body weight measuring means, said body height estimated by said body height estimating means, and said electric resistance value measured by said electric resistance measuring means.

An additional aspect of the present invention is the living body information acquiring apparatus comprising skinfold thickness measuring means composed of a light source for measuring a skinfold thickness of a living body and a photodetector for detecting light which is outgoing from the light source and is diffusely scattered through an interior of said living body.

A still additional aspect of the present invention is the living body information acquiring apparatus comprising:

relative position fixing means fixing a relative position of said skinfold thickness measuring means to said living body substantially constant; and holding means holding a portion of said distance measuring means, said electric resistance measuring means, said skinfold thickness measuring means, and said relative position fixing means.

A still yet supplementary aspect of the present invention is a living body information acquiring method comprising:

a first step of measuring a body weight of a living body;

a second step of measuring a distance between an umbilicus of the living body and body weight measuring means when said living body gets on said weight measuring means;

a third step of estimating a body height of said living body based on said distance obtained in the second step;

a fourth step of measuring an electric resistance value of said living body; and a fifth step of calculating a body fat percentage of said living body, based on said body weight obtained in said first step, said body height obtained in said third step, and said electric resistance value obtained in said fourth step.

Figure 1:
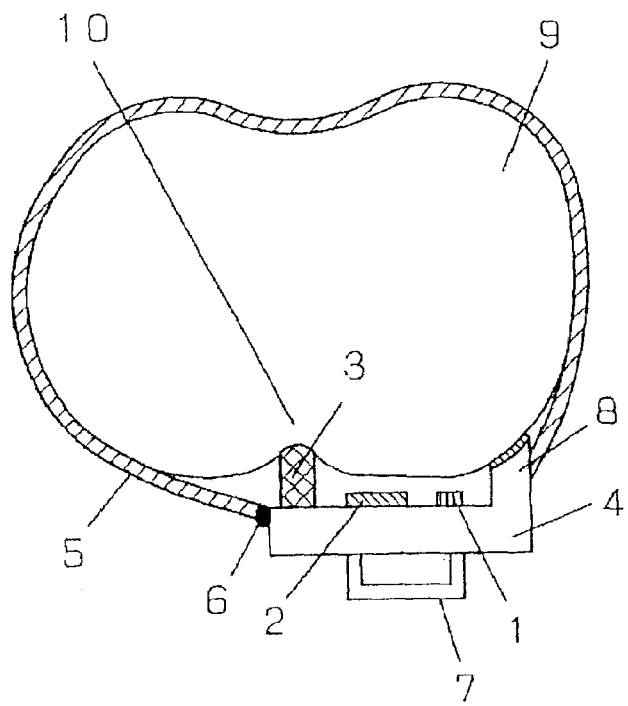
FIG. 1 is a sectional view showing a body fat measuring apparatus according to an embodiment of the present invention.

DESCRIPTION OF REFERENCE NUMERALS 1 light source
2 photodetector
3, 13, 22, 32 protruding part
4 holding means
5 waist measuring means
6 securing part
7, 12, 20 grip part
8 adhering means
9 living body
10 umbilical region
11 bath scale
14 distance measuring means
21, 33, 37 electrodes
23, 34 skinfold thickness measuring means
31 holding part
35 coupling part
36 supporting part

BEST MODE FOR CARRYING OUT THE INVENTION

Embodiments of the present invention will now be described below with reference to FIGS. 1 to 5.

Embodiment 1

FIG. 1 is a sectional view showing a body fat measuring apparatus according to Embodiment 1 of the present invention.

Holding means 4 is provided with a protruding part 3 as relative position fixing means of fixing relative distances of a light source 1 and a photodetector 2 to a living body 9 substantially constant, the light source 1 and the photodetector 2 which constitute skinfold thickness measuring means (an example of living body information acquiring means), adhering means 8 as a second protruding part, and a grip part 7.

In this embodiment, any substances which can emit light passing through the living body may be used as the light source 1, and for example, such substances include an infrared LED having a wavelength of 950 nm, a visible laser having a wavelength of 650 nm, a halogen lamp, a xenon lamp or the like. Among others, the infrared LED having a wavelength of 950 nm or the visible laser having a wavelength of 650 nm is preferred as the light source 1 because of its small size. Further, any devices which can detect the above described light may be used as the photodetector 2, and for example, such devices include a Si-phototransistor, a Si-photodiode, an image sensor, a photo-IC or the like.

The skinfold thickness at an abdominal region is measured by grasping the grip part 7, placing the protruding part 3 onto an umbilical region 10 of the living body 9, irradiating the living body 9 with the light from the light source 1, and detecting the diffusely reflected light from the living body 9. Placing the protruding part 3 onto the umbilical region 10 allows for fixing a relative position of skinfold thickness measuring means to the living body 9, so that the skinfold thickness at a specific position within the abdominal region can be easily measured with high precision.

The adhering means 8 is for improving the adhesion between the living body 9 and the holding means 4 and allows for easily securing the holding means 4 onto the living body 9 as well as preventing the photodetector 2 from being subjected to undesired incoming light from a slit between the living body 9 and the holding means 4. Preferably, a shape of a contacting part between the adhering means 8 and the living body 9 is made to have an oblique section as shown in FIG. 1.

In addition, it is preferable to provide angle adjusting means which can change a contact angle between the living body 9 and the adhering means 8 because curvatures of the abdominal regions vary among individuals.

Further, the holding means 4 is provided with waist measuring means 5. The waist measuring means 5 is in a shape like a string or a belt, and one end thereof is connected to the holding means 4. A circumference of waist can be easily measured by wrapping the waist measuring means 5 around the abdominal region of the living body 9, and then securing the securing means 6 provided at the other end of the waist measuring means 5 to the holding means 4.

The visceral fat obesity has been known for its tendency to easily result in life-style related diseases compared with the subcutaneous fat obesity, and the determination of whether the obesity is an offal fat type or a subcutaneous fat type has been made by the circumference of a waist conventionally, and for example, a type with a circumference of a waist being 85 cm or more has been regarded as the visceral fat obesity. However, the circumference of waist is also affected by the skinfold thickness, so that it is preferable to eliminate the influence of the skinfold thickness in order to accurately make the determination of whether the obesity is an offal fat type or a subcutaneous fat type.

According to a body fat measuring apparatus of this embodiment, a circumference of waist and a skinfold thickness can be simultaneously measured, so that it becomes possible to accurately calculate a circumference of visceral region at the waist by eliminating an influence of the skinfold thickness from the measured circumference of waist. Therefore, a determination whether an obesity is of an offal fat type or a subcutaneous fat type can be made with reliability.

In addition, a living body information acquiring apparatus, which comprises obesity type specifying means of specifying an obesity type of a living body based on a circumference of waist being measured by waist measuring means 5 and a skinfold thickness being measured by the above described skinfold measuring means, also belongs to the present invention. For example, the obesity type specifying means can specify the obesity type by storing a table or calculating formulae therein for specifying the obesity type from the circumference of waist and the skinfold thickness and by utilizing the table and the calculating formulae stored.

In Embodiment 1, a body fat measuring apparatus was used as an example of a living body information acquiring apparatus.

Embodiment 2

Figure 2:
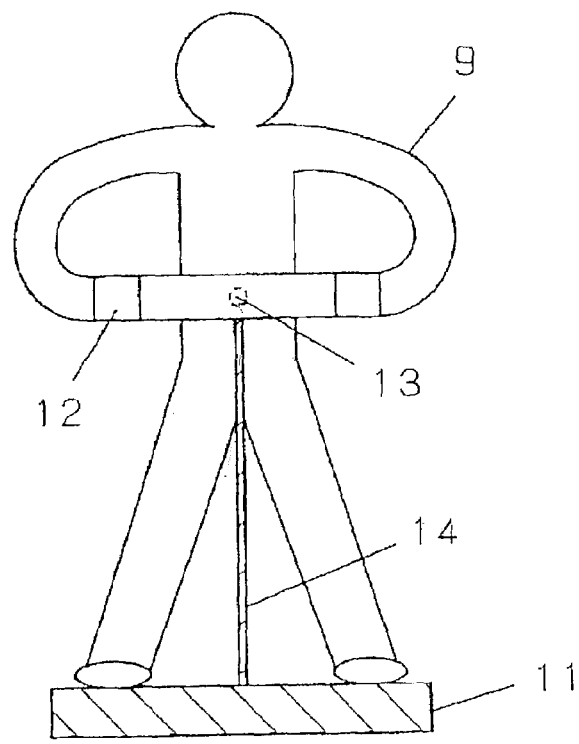
FIG. 2 is a front view showing a body fat measuring apparatus according to another embodiment of the present invention.
Figure 3:
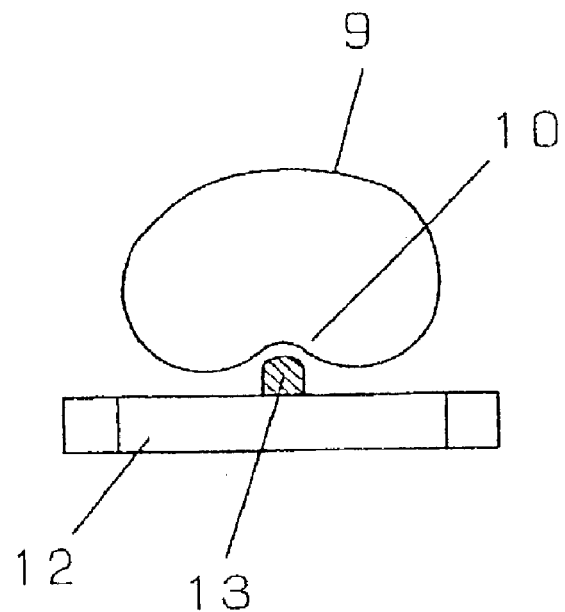
FIG. 3 is a sectional view showing a grip part of a body fat measuring apparatus.

FIG. 2 is a front view showing a body fat measuring apparatus according to Embodiment 2 of the present invention, and FIG. 3 is a sectional view showing a grip part of the body fat measuring apparatus.

A grip part 12 as holding means is provided with a protruding part 13 as relative position fixing means. Distance measuring means 14 which measures a distance between a bath scale 11 as body weight measuring means and the grip part 12 is provided between the bath scale 11 and the grip part 12. The body weight and an umbilicus height can be accurately measured by allowing a living body 9 to get on the bath scale 11, to hold up the grip part 12 and to fix the height of the grip part 12 by contacting the protruding part 13 with the umbilical region 10.

The umbilicus height correlates with the body height, so that the degree of obesity can be estimated with the use of the body weight and the umbilicus height.

The body fat measuring apparatus according to this embodiment eliminates the need for providing a large-scale height meter, so that the miniaturization of the apparatus can be achieved.

In addition, it is preferable to provide electrodes as electric resistance measuring means for the grip part 12 in order to add a function of measuring an electric resistance value between both hands or between both wrists because a body fat percentage can be calculated by the use of the body weight, the umbilicus height, and the electric resistance value. The measurement of the electric resistance value may be performed between both legs or between a hand and a leg.

Further, it is preferable that the distance measuring means 14 is provided with communication means of communicating the information by radio waves, wires or optical communication for example, so that the transmission/reception of the information can be achieved between the bath scale 11 and the grip part 12 each other. This provision enables automatic calculation of the body fat percentage by the use of the body weight, the umbilicus height and the electric resistance value, so that the accurate living body information can be easily acquired.

A living body information apparatus, which comprises body height estimating means of estimating a body height of a living body 9 based on an umbilicus height of the living body 9 when the living body 9 gets on a bath scale 11, and body fat percentage calculating means of calculating a body fat percentage of the living body 9 based on a body weight, an electric resistance value and the estimated body height, also belongs to the present invention. For example, the body fat percentage calculating means allows for calculating the body fat percentage by storing a table or calculating formulae therein for calculating the body fat percentage from the body height, the body weight and the electric resistance value and by utilizing the table and the calculating formulae stored. The calculating means may be a processor and memory connected to an input/output device having as inputs (1) photodector 2, (2) waist measuring means 5, (3) bath scale 11, (4) electrodes 21,33 and 37 (5) skinfold measuring means 23 and 34 and (6) distance measuring means 14.

In Embodiment 2, a body fat measuring apparatus was used as an example of the living body information acquiring apparatus.

Embodiment 3

Figure 4:
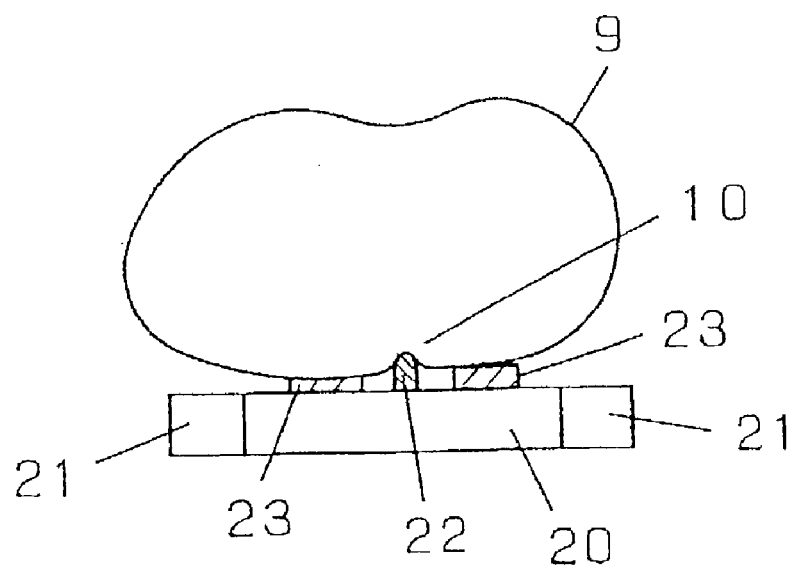
FIG. 4 is a sectional view showing a grip part of a body fat measuring apparatus according to yet another embodiment of the present invention.

FIG. 4 is a sectional view showing a grip part of a body fat measuring apparatus according to Embodiment 3 of the present invention.

A grip part 20 which is holding means is provided with a protruding part 22 as relative position fixing means, skinfold thickness measuring means 23 composed of a light source and a photodetector as in the case of Embodiment 1, and electrodes 21 as electric resistance measuring means. The body fat measuring apparatus according to this embodiment comprises a bath scale (not shown) as in the case of Embodiment 2.

As is the case with Embodiment 1, placing the protruding part 22 onto the umbilical region 10 allows for a position of the skinfold thickness measuring means 23 to be fixed, so that the skinfold thickness at a specific position of the abdominal region can be measured with ease and high precision.

The skinfold thickness of the abdominal region has been known for its high correlation with the body fat percentage, so that the body fat percentage can be measured with high precision by calculating the body fat percentage from the body weight and the skinfold thickness with the use of the apparatus for measuring the body fat according to this embodiment.

In addition, the body fat percentage can be measured with higher precision by the use of the electric resistance value between both hands measured by the electrodes 21, the body weight, and the skinfold thickness.

In this case, it is preferable to provide a function of transmitting/receiving the information between the skinfold thickness measuring means 23 and the bath scale each other.

In Embodiment 3, a body fat measuring apparatus was used as an example of the living body information acquiring apparatus.

Embodiment 4

Figure 5:
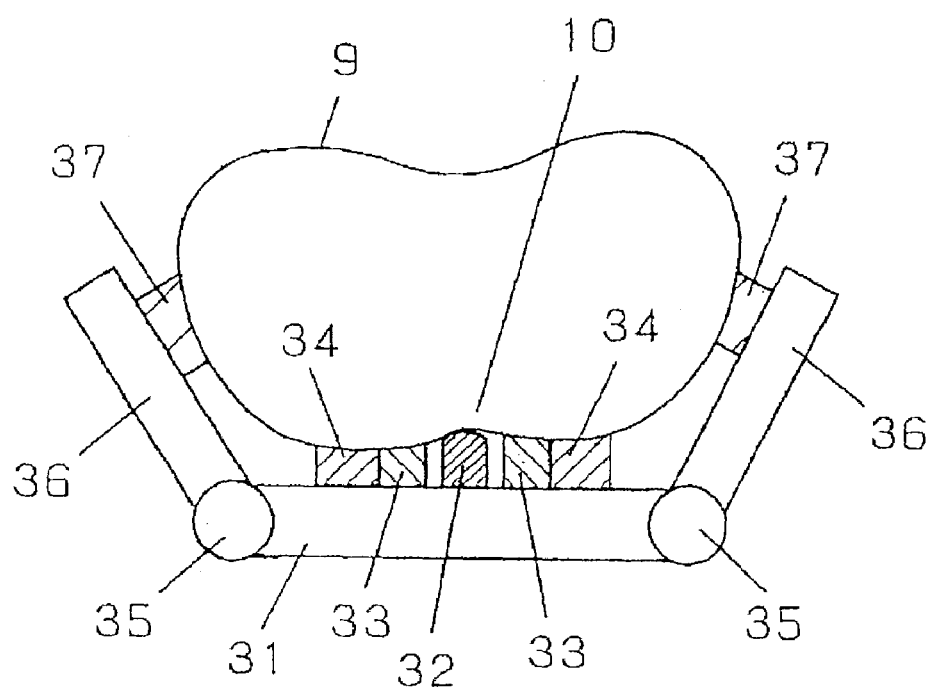
FIG. 5 is a sectional view showing a body fat measuring apparatus according to yet another embodiment of the present invention.

FIG. 5 is a sectional view showing a body fat measuring apparatus according to Embodiment 4 of the present invention.

A protruding part 32 as relative position fixing means, electrodes 33 as electric resistance measuring means, and skinfold thickness measuring means 34 composed of a light source and a photodetector as in the case of Embodiment 1 are provided on a holding part 31 which is regarded as holding means. A supporting part 36 is provided with electrodes 37 regarded as the electric resistance measuring means, and the supporting part 36 and the holding part 31 are connected with a coupling part 35.

In this embodiment, the setting position and the number of the skinfold thickness measuring means 34 as well as the setting positions and the numbers of the electrodes 33 and the electrodes 37 are not limited to the above described values, thus the electrodes 37 may be positioned to come into contact with a back of the living body 9.

Next, a method for calculating an offal fat amount using the body fat measuring apparatus according to this embodiment will be briefly described.

The protruding part 32 is placed on the umbilical region 10 such that the electrodes 33 and the electrodes 37 come into contact with the abdominal region of the living body 9.

The skinfold thickness of the abdominal region is calculated by the skinfold thickness measuring means 34 provided on the holding part 31, and then the electric resistance value of the abdominal region is determined by the use of the electrodes 33 and the electrodes 37. The electric resistance value tend to become larger as the fat thickness increases because electricity is less apt to flow through the fat when the fat thickness becomes larger, so that a sum of the subcutaneous fat amount and the offal fat amount in the vicinity of the abdominal region can be determined by measuring the electric resistance value between the electrode 33 and the electrode 37.

In this case, the sum of the subcutaneous fat amount and the offal fat amount of each person is determined by the use of an X-ray CT or an MRI for example, and then correspondences (Correlation 1) between the electric resistance value and the sum of the subcutaneous fat amount and the offal fat amount are made in advance. Further, a subcutaneous fat amount of each person is also determined using the X-ray CT or the MRI for example, and correspondences (Correlation 2) between the subcutaneous fat amount and the skinfold thickness calculated by the skinfold thickness measuring means 34 are made in advance.

Then, the sum of the subcutaneous fat amount and the offal fat amount in the vicinity of the abdominal region of the living body 9 is calculated from the electric resistance value actually measured and Correlation 1, while the subcutaneous fat amount in the vicinity of the abdominal region of the living body 9 is calculated from the skinfold thickness measuring means 34 and Correlation 2.

Next, the offal fat amount of the living body 9 can be calculated by subtracting the subcutaneous fat amount calculated using Correlation 2 from the sum of the subcutaneous fat amount and the offal fat amount calculated with the use of the above described Correlation 1.

In this way, as in the case of Embodiment 1, placement of the protruding part 32 onto the umbilical region 10 makes it possible to fix the relative position of the skinfold thickness measuring means 34 to the living body 9 substantially constant as well as to fix the position of the electrodes 33, and also make it possible to fix the position of the electrodes 37 by the supporting part 36, so that the skinfold thickness and the electric resistance value at a specific position of the abdominal region can be measured with ease and high precision by the use of a simple configuration.

A living body information acquiring apparatus, which comprises total fat amount calculating means of calculating a total fat amount along a pathway crossing an interior of the living body 9 based on the measured electric resistance value and offal fat amount calculating means of calculating the offal fat amount along the above described pathway based on the skinfold thickness measured by the skinfold thickness measuring means 34 and the total fat amount calculated by the total fat amount calculating means, also belongs to the present invention. For example, the total fat amount calculating means can calculate the total fat amount by storing the above described correlations and utilizing the correlations.

In addition, the subcutaneous fat amount and the skinfold thickness have a predetermined relationship between them, while the offal fat amount and the offal fat thickness also have a predetermined relationship between them.

Further, in Embodiment 4, a body fat measuring apparatus was used as an example of the living body information acquiring apparatus.

The above described embodiments have shown skinfold thickness measuring means which optically measures the skinfold thickness, but do not intend to limit the present invention, thus the skinfold thickness may be measured by the use of an ultrasonic system. However, measurement of the skinfold thickness using an optical system is preferable because there is no need to interpose water or a jelly-like solvent between a living body and a skinfold thickness measuring means.

In addition, the holding means may be provided with means of securing fingers or wrists to acquire the living body information such as blood pressures, pulse values, concentrations of oxygen saturation, hemoglobin concentrations, blood glucose levels, and temperatures.

It is also preferable to provide a display for the holding means in order to display calculation results concerning the living body information, because the living body 9 can easily look at the measurement results.

The above described embodiments have shown the measurement of the skinfold thickness at the abdominal region, but do not intend to limit the present invention, thus the above described measurement may be utilized for measuring the skinfold thickness of a brachial region, a femoral region, a scapular region or the like.

Further, it is preferable to provide transferring means for the weight measuring means or holding means of the above described body fat measuring apparatus in order to connect with medical institutions and service facilities etc. through telephone lines or communication lines. This is extremely useful when continuously performing the day-to-day health care.

According to the above described embodiments, living body information such as a degree of obesity, a body fat percentage, a skinfold thickness, and offal fat can be measured with ease and high precision by the use of a very compact configuration. Further, topical living body information concerning an abdominal region, a brachial region, a femoral region, a scapular region or the like can be obtained as well.

INDUSTRIAL APPLICABILITY

As is clear from the above description, the present invention can provide a living body information acquiring apparatus of acquiring the living body information of the living body, in which a distance between a living body and living body information acquiring means is fixed substantially constant.

Further, the present invention can provide a living body information acquiring method for calculating an offal fat amount of a living body.

Further, the present invention can provide a living body information acquiring apparatus for calculating an offal fat amount of a living body.

Still further, the present invention can provide a living body information acquiring apparatus and a living body information acquiring method which specify the type of obesity of a living body.

Still further, the present invention can provide a living body information acquiring apparatus for measuring an umbilicus height of a living body.

In addition, the present invention can provide a living body information acquiring method and a living body information acquiring apparatus which calculate a body fat percentage of the living body by measuring an umbilicus height of a living body and utilizing the umbilicus height.

The invention claimed is:

1. A living body information acquiring apparatus comprising:
living body information acquiring means acquiring living body information of a living body,
relative position fixing means fixing a relative position of said living body information acquiring means to an abdominal region of said living body substantially constant,
holding means holding said living body information acquiring means and said relative position fixing means, and
waist measuring means measuring a circumference of waist of said living body, wherein said living body Information is a skinfold thickness at a waist position of said living body, and said relative position fixing means is means fixing a distance between an umbilicus of said living body and said living body information acquiring means substantially constant.

2. A living body information acquiring apparatus comprising:
living body information acquiring means acquiring living body information of a living body,
relative position fixing means fixing a relative position of said living body information acquiring means to an abdominal region of said living body substantially constant, and
holding means holding said living body information acquiring means and said relative position fixing means,
wherein said relative position fixing means has a protruding part, an end portion of said protruding portion is situated closer to said living body than a side of said holding means facing said living body when said apparatus is acquiring living body information.

3. A living body information acquiring apparatus comprising:
living body information acquiring means acquiring living body information of a living body,
relative position fixing means fixing a relative position of said living body information acquiring means to an abdominal region of said living body substantially constant, and
holding means holding said living body information acquiring means and said relative position fixing means,
wherein said living body information acquiring means has a light source for measuring a skinfold thickness of a living body and a photodetector for detecting light Which is outgoing from the light source and is diffusely scattered through an interior of said living body.

4. The living body information acquiring apparatus according to claim 3, wherein:
said relative position Fixing means has a first protruding part while said holding means has a second protruding part;
a body of said holding means, said first protruding part, and said second protruding part form a space; and
said living body information acquiring means is secured to the body of said holding means within said space.

5. A living body information acquiring apparatus comprising:
waist measuring means measuring a circumference of waist of a living body;
skinfold thickness information capturing means capturing information of a skinfold thickness at a waist position of said living body; and
obesity type specifying means in which an obesity type of the living body whose circumference of waist is measured by said waist measuring means is specified based on said circumference of waist measured by said waist measuring means and information about said skinfold thickness captured by said skinfold thickness information capturing means.

6. A living body information acquiring apparatus comprising body weight measuring means measuring a body weight of a living body and distance measuring means measuring a distance between an umbilicus of the living body and said body weight measuring means when the living body is on said body weight measuring means.

7. The living body information acquiring apparatus according to claim 6 comprising electric resistance measuring means which is held by both hands of the living body getting on said body weight measuring means and which measures an electric resistance value of the living body.

8. The living body information acquiring apparatus according to claim 7 comprising:
  body height estimating means estimating a body height of a living body getting on said body weight measuring means, based on the distance between an umbilicus of the living body and said body weight measuring means when the living body is on said body weight measuring means; and
  body fat percentage calculating means calculating a body fat percentage of said living body, based on said body weight measured by said body weight measuring means, said body height estimated by said body height estimating means, and said electric resistance value measured by said electric resistance measuring means.

9. The living body information acquiring apparatus according to any of claims 6 to 8 comprising skinfold thickness measuring means composed of a light source for measuring a skinfold thickness of a living body and a photodetector for detecting light which is outgoing from the light source and is diffusely scattered through an interior of said living body.

10. The living body information acquiring apparatus according to claim 9 comprising:
  relative position fixing means fixing a relative position of said skinfold thickness measuring means to said living body substantially constant; and
  holding means holding a portion of said distance measuring means, said electric resistance measuring means, said skinfold thickness measuring means, and said relative position fixing means.

11. A living body information acquiring method comprising:
  a first step of measuring a body weight of a living body;
  a second step of measuring a distance between an umbilicus of the living body and body weight measuring means when said living body gets on said weight measuring means;
  a third step of estimating a body height of said living body based on said distance obtained in the second step;
  a fourth step of measuring an electric resistance value of said living body; and
  a fifth step of calculating a body fat percentage of said living body, based on said body weight obtained in said first step, said body height obtained in said third step, and said electric resistance value obtained in said fourth step.

* * * * *